US 8,714,156 B2

(12) United States Patent
Cooke et al.

(10) Patent No.: US 8,714,156 B2
(45) Date of Patent: May 6, 2014

(54) VENTILATOR FOR RAPID RESPONSE TO RESPIRATORY DISEASE CONDITIONS

(75) Inventors: Richard Henry Cooke, Essex (GB); Nicholas Ong, Bellevue, WA (US); Roy Hays, Seattle, WA (US)

(73) Assignee: Spacelabs Healthcare, LLC, Issaquah, WA (US)

( * ) Notice: Subject to any disclaimer, the term of this patent is extended or adjusted under 35 U.S.C. 154(b) by 1348 days.

(21) Appl. No.: 11/871,341

(22) Filed: Oct. 12, 2007

(65) Prior Publication Data
US 2008/0168990 A1    Jul. 17, 2008

Related U.S. Application Data

(60) Provisional application No. 60/829,502, filed on Oct. 13, 2006.

(51) Int. Cl.
*A62B 9/02* (2006.01)
*A62B 7/00* (2006.01)
*A62B 7/04* (2006.01)

(52) U.S. Cl.
USPC ............ 128/205.24; 128/205.11; 128/204.26; 128/204.18

(58) Field of Classification Search
CPC .............. A61M 16/00; A61M 2016/0069; A61M 2016/006; A61M 2016/00; A61M 2016/12; A61M 2016/122; A61M 2016/125; A61M 2016/127; A61M 2016/20; A61M 2016/201; A61M 2016/206; A61M 2016/207; A61M 2016/208; A61M 16/12; A61M 16/10; A61M 16/20; A62B 9/00; A62B 9/02; A62B 9/022; A62B 7/00–7/04

USPC ............... 128/204.18, 204.21–204.23, 128/204.25–204.26, 204.29–205.11, 205.24
See application file for complete search history.

(56) References Cited

U.S. PATENT DOCUMENTS

| | | | |
|---|---|---|---|
| 3,682,166 A | 8/1972 | Jacobs | |
| 3,726,274 A * | 4/1973 | Bird et al. ................ | 128/205.24 |
| 4,033,343 A | 7/1977 | Jones | |
| 4,487,207 A | 12/1984 | Fitz | |
| 4,587,967 A | 5/1986 | Chu et al. | |
| 4,617,637 A | 10/1986 | Chu et al. | |
| 4,622,963 A | 11/1986 | Ansite | |
| 4,682,591 A * | 7/1987 | Jones ....................... | 128/204.25 |
| 4,726,366 A | 2/1988 | Apple et al. | |
| 4,823,788 A | 4/1989 | Smith et al. | |
| 4,957,107 A | 9/1990 | Sipin | |
| 4,971,049 A | 11/1990 | Rotariu et al. | |
| 5,107,830 A | 4/1992 | Younes | |
| 5,211,171 A | 5/1993 | Choromokos | |
| 5,303,699 A | 4/1994 | Bonassa et al. | |
| 5,493,488 A | 2/1996 | Castle et al. | |

(Continued)

OTHER PUBLICATIONS

International Search Report for PCT/US07/62747, Mar. 3, 2008.

(Continued)

*Primary Examiner* — Rachel Young
(74) *Attorney, Agent, or Firm* — Novel IP

(57) ABSTRACT

The present invention relates generally to the field of ventilators, and, more specifically, to a ventilator system that addresses respiratory distress due to the onset of an epidemic or pandemic disease state. In particular, the present invention is a ventilator system that can be manufactured quickly with minimal skill requirements and employed rapidly in response to epidemic respiratory disease conditions.

24 Claims, 5 Drawing Sheets

(56) References Cited

U.S. PATENT DOCUMENTS

| | | | |
|---|---|---|---|
| 5,503,145 | A | 4/1996 | Clough |
| 5,623,921 | A | 4/1997 | Kinsinger et al. |
| 5,794,986 | A | 8/1998 | Gansel et al. |
| 5,862,802 | A | 1/1999 | Bird |
| 6,000,396 | A | 12/1999 | Melker et al. |
| 6,041,777 | A * | 3/2000 | Faithfull et al. .......... 128/200.24 |
| 6,131,571 | A * | 10/2000 | Lampotang et al. ..... 128/204.21 |
| 6,523,538 | B1 | 2/2003 | Wikefeldt |
| 6,604,523 | B2 | 8/2003 | Lurie et al. |
| 6,609,518 | B2 * | 8/2003 | Lamb ...................... 128/204.25 |
| 7,000,612 | B2 | 2/2006 | Jafari et al. |
| 7,458,390 | B2 * | 12/2008 | Gossweiler .................. 137/494 |
| 2002/0104537 | A1 | 8/2002 | Banner et al. |
| 2003/0037786 | A1 * | 2/2003 | Biondi et al. ............ 128/204.21 |
| 2005/0005936 | A1 | 1/2005 | Wondka |
| 2005/0121035 | A1 | 6/2005 | Martin |
| 2005/0205098 | A1 * | 9/2005 | Lampotang et al. ..... 128/207.18 |
| 2006/0048781 | A1 * | 3/2006 | Nawata .................... 128/204.23 |
| 2006/0144396 | A1 | 7/2006 | DeVries et al. |
| 2006/0180149 | A1 * | 8/2006 | Matarasso ................ 128/204.18 |
| 2007/0193579 | A1 * | 8/2007 | Duquette et al. ......... 128/204.18 |
| 2008/0216836 | A1 * | 9/2008 | Ottestad .................. 128/204.28 |

OTHER PUBLICATIONS

International Search Report fot PCT/US07/6274, Mar. 3, 2008, International Search Aurhotity.

International Search Report for PCT/US07/081198, Apr. 16, 2008, International Search Authority.

\* cited by examiner

VENTILATOR FOR RAPID RESPONSE TO RESPIRATORY DISEASE CONDITIONS

CROSS-REFERENCE

The present invention relies on, for priority, U.S. Provisional Application No. 60/829,502, filed on Oct. 13, 2006.

FIELD OF THE INVENTION

The present invention relates generally to the field of ventilators, and, more specifically, to a ventilator system that addresses respiratory distress due to the onset of an epidemic or pandemic disease state. More specifically, the present invention is a ventilator system that has control and range of operation so that it meets the needs of acute respiratory distress syndrome (ARDS) patients in various stages of a compromised state through to recovery. In particular, the present invention is a ventilator system that can be manufactured quickly with minimal skill requirements and employed rapidly in response to epidemic respiratory disease conditions.

BACKGROUND OF THE INVENTION

Respiratory distress may be brought on by the onset of an epidemic of an infectious agent in an otherwise healthy population. Respiratory distress can be caused by several disease states, including, but, not limited to Severe Acute Respiratory Syndrome (or "SARS") and Avian Influenza ("Bird Flu"). Severe Acute Respiratory Syndrome (or "SARS"), a serious form of pneumonia resulting in respiratory distress and sometimes death, has become an emerging epidemic threat. Every new case of SARS and/or Avian Influenza reported still has the potential to spark another outbreak and even worse, a global pandemic. The most characteristic symptoms of SARS include fever, cough, difficulty breathing and/or other respiratory symptoms. In most cases, supportive care such as the use of supplemental oxygen, chest physiotherapy, and/or mechanical ventilation is needed. Avian Influenza is another emerging epidemic threat that results in severe respiratory distress with an even faster onslaught of symptoms.

Respiratory distress, among other symptoms, includes an impaired ability of the patient to maintain efficient oxygenation. Regardless of the epidemic or infectious agent, however, the respiratory discomfort of critically ill persons that is associated with these disease conditions can be eased, and in many cases recovery hastened, by connecting the patient to a ventilator. Conventionally, to ease impaired respiration, a patient is sedated and mechanically ventilated using either pressure or volume ventilation.

A typical ventilator operates either by forcing pressurized gas (as in a positive-pressure ventilator) into the lungs or by expanding the chest cavity of the patient to draw gas into the lungs (as in a negative-pressure ventilator) under a pre-determined and operator input schedule of gas composition, pressure, and flow pattern.

Currently, conventional ventilators employ microprocessors to control ventilation parameters and to contain pressure and flow measurement transducers, which provide electrical data (via analog-to-digital converters) to the microprocessors for display of monitored parameters and for alarm activation or alert conditions.

In addition, conventional ventilators require either the use large fabrication machinery with a complicated set-up to produce the various metal parts or advanced tooling and molding processes that are necessary to produce highly durable plastic parts. As new features and ventilating modes are added, the complexity of operation increases as the existing controls and display areas are burdened with the requirement of facilitating input and display of the new features. Thus, conventional ventilators are complex devices and are costly to manufacture and operate.

In addition, conventional ventilator systems are designed to handle a wide range of patient conditions. For example, a patient in the intensive care unit of a hospital typically is overcome by a number of disorders or disease states, in which the body systems are in danger of failing. The intensive care unit must also be able to handle a wide range of patients with a wide range of complaints, including surgery, trauma, heart disease, infection, etc. Thus, conventional ventilators have a large number of operational modes, produced by a complicated set of components, requiring a skilled technician to set up the system.

Therefore, what is needed is a ventilator that has physical and operational simplicity. What is also needed is a ventilator that is manufactured with materials that are readily available. What is also needed is a ventilator that can be fabricated with simpler, low-cost tooling and methods.

In addition, what is needed is a ventilator that is capable of responding to respiratory distress brought on by an infectious agent in an otherwise healthy population. What is also needed is a ventilator that is capable of responding to varying patient needs. What is also needed is a ventilator that is capable of meeting the needs of ARDS patients ranging from a critical state until the patient can be safely weaned from the ventilator.

What is also needed is a ventilator that can be manufactured easily and cost effectively at any time the onset of a respiratory epidemic is detected, in scalable volumes.

In addition, what is needed is a ventilator that can be manufactured in any location quickly, prior to the peak period of the epidemic. What is also needed is a ventilator that can ease the burden on ventilator resources in certain communities.

SUMMARY OF THE INVENTION

The present invention is directed toward controllable mechanical ventilators. In one embodiment, the controllable mechanical ventilator comprises a gas input connected to a gas reservoir, an inhalation conduit connected to said gas reservoir for receiving gas and directing it to a patient interface, a flow control valve operable to control the flow of gas from the inhalation conduit to an air entrainment area, wherein said air entrainment area is connected, via a first conduit and a second conduit, to a port for receiving atmospheric air, a patient interface connected to said air entrainment area by a conduit; and a gas shut-off mechanism that senses a pressure state in said inhalation conduit. Optionally, a valve is located in the first conduit to prevent air from passing out of the port and into the atmosphere. Optionally, the second conduit has a first end connected to said first conduit and a second end connected to said air entrainment area and wherein the second conduit has a diameter that narrows from said first end to said second end, thereby having a diameter that is larger at said first end than at said second end. Optionally, the amount of atmospheric air delivered through said patient interface can be modified by blocking said port.

In another embodiment, the present invention comprises a gas input connected to a gas reservoir, a patient flow control valve operably connected to control gas input from said gas reservoir via an inhalation conduit, a patient interface separated from said inhalation conduit by said flow control valve, a gas shut-off mechanism that senses a pressure state in said inhalation conduit, wherein said ventilator is capable of responding to varying patient need via at least one control.

In another embodiment, the controllable mechanical ventilator of the present invention comprises a gas input connected to a gas reservoir, a patient flow control valve operably connected to control gas input from said gas reservoir via an inhalation conduit, a patient interface, separated from said inhalation conduit by said flow control valve, a gas shut-off mechanism that senses a pressure state in said inhalation conduit, wherein said ventilator further comprises means for controlling at least one of: PIP, PEEP, the level of oxygenation and respiration rate.

Optionally, the ventilator further comprises a humidifying filter for trapping moisture and heat and sterilizable material. Optionally, the patient flow control valve is adjustable to provide for a specific gas flow rate and the gas flow rate can be set to at least one of adult, pediatric, and infant modes. Optionally, PIP is in the range of 20 cm $H_2O$ to 35 cm $H_2O$. Optionally, the gas input further comprises a gas interface for connection to a pressurized gas source. Optionally, the patient interface further comprises a patient interface for accepting exhaled gas from the patient and a patient interface for delivering gas to the patient and is one of a breathing mask assembly, endotracheal tube, or laryngeal mask airway device.

Optionally, the flow control valve is in structural communication with a knob, capable of being physically manipulated to control breath rate. Optionally, the ventilator further comprises an expiratory conduit and expiratory valve operably connected to the patient interface or a pressure detector and an alarm circuit operably connected to the pressure detector, wherein said alarm circuit generates an alarm signal based upon a change in pressure detected by said pressure detector. Optionally, the respiration rate is varied by keeping the inspiratory time fixed and varying the expiratory time and PEEP is a variable control ranging from 5 cm $H_2O$ to 20 cm $H_2O$. Optionally, the ventilator further comprises an integrated pressure gauge, located proximate to the patient interface, for measuring and displaying the instantaneous airway pressure in the circuit.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
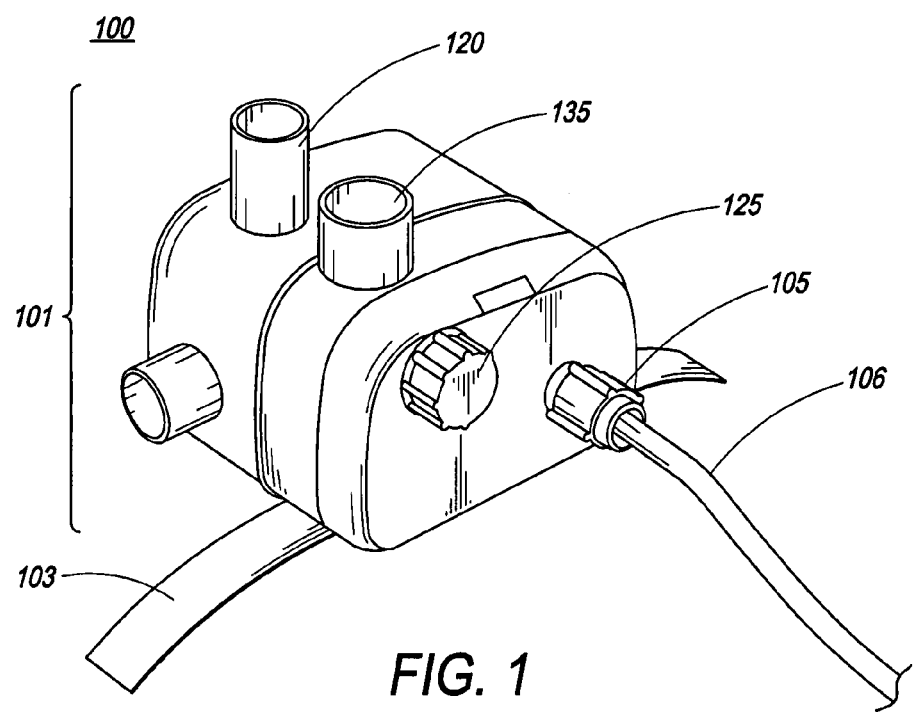
FIG. 1 is an illustration of a first embodiment of the ventilator of the present invention.

The present invention is directed towards a ventilator system that can be manufactured quickly with minimal skill requirements and rapidly deployed in response to epidemic respiratory disease conditions.

The present invention is directed towards multiple embodiments. Language used in this specification should not be interpreted as a general disavowal of any one specific embodiment or used to limit the claims beyond the meaning of the terms used therein. Reference will now be made in detail to specific embodiments of the invention. While the invention will be described in conjunction with specific embodiments, it is not intended to limit the invention to one embodiment.

In one embodiment, the present invention is directed towards a ventilator having a minimal number of controls. In one embodiment, the present invention is directed towards a ventilator that is used to give ventilation or mechanical breathing to a patient suffering ARDS. In one embodiment, the mechanical ventilation of the present invention is based on pressure control and has variable pressure, breathing rate, and oxygenation.

Preferably, the ventilator is rapidly deployable. Still preferably, the ventilator is as easy and intuitive to operate as possible. Still preferably, the ventilator is capable of sustaining at least 75% of epidemic respiratory distress victims who require assisted ventilation until resuming normal breathing.

In another embodiment, the present invention is directed towards a simple, safe and effective means for delivering oxygen-enriched air to the ventilator when the ventilator is used in emergency and overflow facilities outside the standard hospital environment.

In another embodiment, the present invention is directed towards a rapid response ventilator system that further provides for the use of a humidifying filter for trapping moisture and heat for patients on an extended use.

In another embodiment, the present invention is directed towards a rapid response ventilator system that is capable of being manufactured and distributed in sufficient volume and at very low cost in a substantial part of the world.

In yet another embodiment, the present invention is directed towards a rapid response ventilator system that can be safely and responsibly disposed of after use.

The present invention is also directed towards a ventilator that has physical and operational simplicity. In addition, the present invention is directed towards a ventilator, which, in one embodiment, is manufactured with materials that are readily available. In other embodiments, the ventilator of the present invention can be fabricated with simple, low-cost tooling and methods.

In one embodiment, the ventilator of the present invention is a simple, moulded device that requires little or no adjustment. The simple, no adjustment moulded device is advantageous in that it poses no additional risk to the patient. In one embodiment, the ventilator of the present invention has limited controls.

In one embodiment, the ventilator of the present invention is manufactured using pre-fabricated tooling for storage at strategic manufacturing sites.

In one embodiment, the ventilator of the present invention is manufactured using tooling fabricated from less durable material at the onset of an epidemic. In one embodiment, the fabrication material includes, but is not limited to, aluminium. It should be understood by those of ordinary skill in the art that any number of tooling materials and tooling kit manufacturing processes may be used in the present invention, including, but, not limited to, bronze sintering and steel fabrication. In one embodiment, the choice of tooling material and kit fabrication selected depends upon the needs of the population and the epidemic and/or pandemic situation. For example, but, not limited to such example, the volume of devices needed may be an indicator of which materials should be used for the tooling and the tooling kit processes.

In one embodiment, the ventilator of the present invention is manufactured using parts that are fabricated in an automated system. Thus, in this embodiment, no tooling is actually created.

In one embodiment, the ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel.

In one embodiment, the ventilator of the present invention is manufactured using tooling fabricated from a material of lower durability than steel at the onset of an epidemic. In one embodiment, the material of lower durability is aluminium. Preferably, the materials are readily accessible to produce a more limited number of units for more localized outbreaks of disease and the tooling is designed such that it can be manufactured fairly rapidly.

In one embodiment, the ventilator of the present invention is manufactured using parts that are fabricated in an automated system directly from design documentation. Thus, no tooling is actually created. This embodiment is particularly useful for supporting remote areas where the ultimate goal is to transport patients to larger centres while still providing temporary respiratory support. Advantageously, in this embodiment, the manufacturing method allows for the ventilators of the present invention to be produced on demand without the time it takes to manufacture the tooling.

In each of the manufacturing embodiments described above, assembly is simple and does not require highly specialized skills or training. The ventilator can thus be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded or disrupted.

In one embodiment, the ventilator of the present invention is operable in a plurality of modes, including adult, pediatric, and infant. In one embodiment, an operator selects a mode by adjusting the inspired gas flow rate, thus affecting the inspiratory time, or the time to reach the pre-set maximum pressure.

In one embodiment, the maximum pressure is pre-set by the operator. In one embodiment, the ventilator is operated at a maximum pressure suitable for most patients without causing any patient injury. In one embodiment, the ventilator operates in a pressure range of 10 cm $H_2O$ to 70 cm $H_2O$. In another embodiment, the ventilator can provide pressure-controlled ventilation up to a pre-set pressure of 20 cm $H_2O$. In another embodiment, the ventilator can provide pressure-controlled ventilation up to a pre-set pressure of 25 cm $H_2O$. In yet another embodiment, the ventilator can optionally provide a venturi to give at least 60% oxygen. It should be noted here that any number of distinct pressures may be set by the operator depending upon individual patient assessment and/or need.

In another embodiment, the ventilator of the present invention is capable of responding to patient need. More specifically, in one embodiment, if a patient begins to resume breathing spontaneously, the ventilator of the present invention is capable of entering a passive mode. In another embodiment, if a patient fails to maintain spontaneous unassisted breath, the ventilator begins to operate and assist with oxygen delivery to the patient.

In one embodiment the present invention is directed towards a disposable ventilator. In another embodiment, the present invention is a limited use system wherein the limitations of use may include one of a plurality of limitations, including singular patient use, run-time, or calendar time. In one embodiment, the present invention is a single patient-use, disposable ventilator with no specific life span.

FIG. 1 is an illustration of a first embodiment of the ventilator of the present invention. In one embodiment, ventilator 100 comprises main housing 101 for housing ventilator components. In one embodiment, ventilator 100 is disposable. In another embodiment, ventilator device 100 is intended for single patient use. In yet another embodiment, ventilator 100 is intended for multiple-patient use, and thus, can be re-used. Preferably, ventilator devices intended for re-use are designed and manufactured such that they can be easily dismantled and cleaned.

In another embodiment, ventilator 100 is manufactured using materials that can be sterilized at a preferred sterilization temperature of 138° C., or the standard temperature of an autoclave. These materials include high temperature plastics, which require more advanced tooling. In one multiple-use embodiment, the ventilator is fabricated with a plastic material with a low melting point, thus allowing its manufacture with cost effective tooling.

In one embodiment, the rapid response ventilator of the present invention is manufactured with connectable parts. The connectable parts of the ventilator can be attached by various methods, either fixedly or removably, such as but not limited to gluing, screwing, or welding, or any other suitable means of connecting tooling parts as are well known to those of ordinary skill in the art.

Ventilator 100 further comprises flow control valve or breathing rate control knob 125, alarm/battery activation tag 103, at least one patient interface or connection port 120, and gas supply connection port 105 that connects to a gas source [not shown] through hose 106.

In one embodiment of the ventilator of the present invention, the breathing rate control knob 125 is the only control that is required to be adjusted by the operator. The breathing rate control knob 125 can be adjusted to allow for various modes of operation, including but not limited to adult mode, pediatric mode, and infant mode. As described above, an operator selects a mode by adjusting the inspired gas flow rate, thus affecting the inspiratory time, or the time to reach the pre-set maximum pressure.

Referring back to FIG. 1, to begin using the rapid response ventilator 100 of the present invention, the operator must first remove the ventilator from its packaging, which is preferably sterile. In one embodiment, the ventilator 100 is then mounted in a safe and stable position located above, but proximate to the patient. The operator then removes the alarm activation tag 103 from the battery of the ventilator by pulling as indicated.

In one embodiment, once the ventilator is unpackaged and positioned, the operator, or any other qualified and trained personnel, sedates and intubates the patient. The ventilator 100 is then connected to the patient's endotracheal tube using a standard breathing circuit and, optionally, a humidifying filter (not shown) at the patient connection point 120. In another embodiment, ventilator 100 is connected to the patient via a breathing mask assembly at patient connection point 120. In yet another embodiment, ventilator 100 is connected to the patient via a laryngeal mask airway (LMA) device. The various patient connection devices for delivering oxygen to the patient are described in greater detail below with respect to FIGS. 3 and 5. The operator then sets the ventilation control via the breathing rate control knob 125. Preferably, the patient's physical dimensions, such as but not limited to height and weight, are employed to determine the breathing rate. The oxygen supply hose 106, connected at gas supply port 105 is then connected to an oxygen source (not shown) to enable ventilator operation.

Ventilator 100 also comprises exhaust port 135, the operation of which is described in greater detail below with respect to FIG. 3. In one embodiment, the oxygen source operates at a pressure ranging from 40 PSI to 70 PSI. The Positive End-Expiratory Pressure (hereinafter "PEEP") control is then set as indicated by the patient's oxygenation indications. PEEP refers to the residual positive pressure that remains in the airway at the end of the expiratory cycle. It is employed to prevent the lung from fully collapsing after each breath, thus improving gas exchange in the lung.

Ventilation is continued with frequent observation of alarm status (described below) and patient oxygenation. In one embodiment, when ventilation is complete or discontinued, the ventilator and breathing circuit components are sealed in a disposable bag and taken to the nearest disposal collection point for proper disposal. In another embodiment, when ventilation is complete or discontinued, the ventilator and breathing circuit components are appropriately sterilized and re-packaged for subsequent use, as described above.

Figure 2:
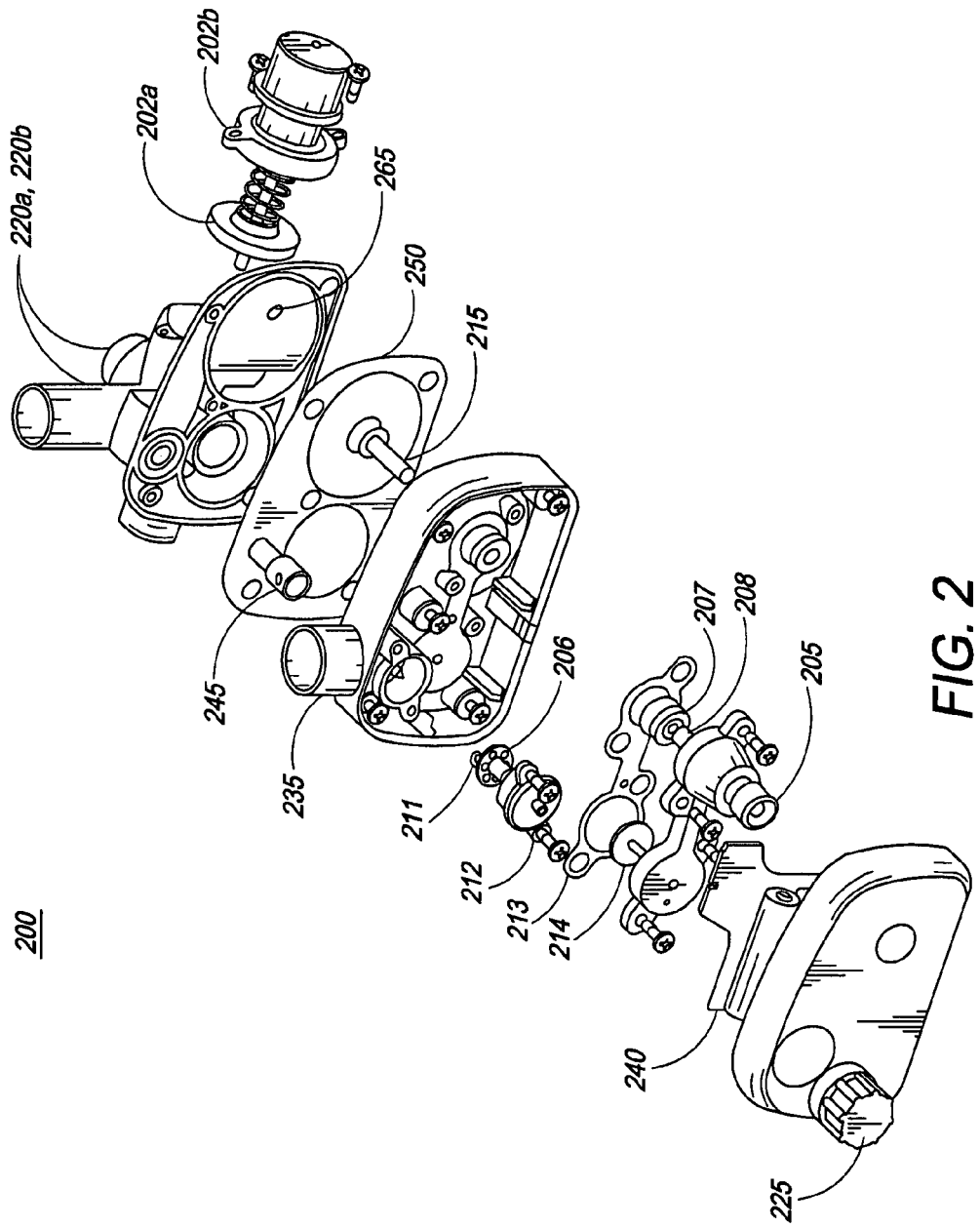
FIG. 2 is a schematic diagram of the system components of a first embodiment of the ventilator of the present invention.

FIG. 2 is a detailed illustration of the system components of a first embodiment of the ventilator of the present invention. In one embodiment, ventilator 200 comprises patient interface or connection port 220, gas over-pressure relief valve 202a and valve cover 202b, leak jet 265, first diaphragm actuator 250, actuator path or inhalation conduit 215, jet disc 206, bellows seal 207, first seal 208, compressed gas interface 205, branch conduit 245, "O"-ring 211, first jet cover 212, top cover seal 213, electronics actuator 214, printed circuit board (PCB) 240, breathing rate control knob 225, and exhaust port 235. In an optional embodiment, ventilator 200 further comprises a venturi (not shown).

In one embodiment, patient interface 220 further comprises patient interface 220a for accepting air from the patient and patient interface 220b for delivering oxygen to the patient.

Figure 3:
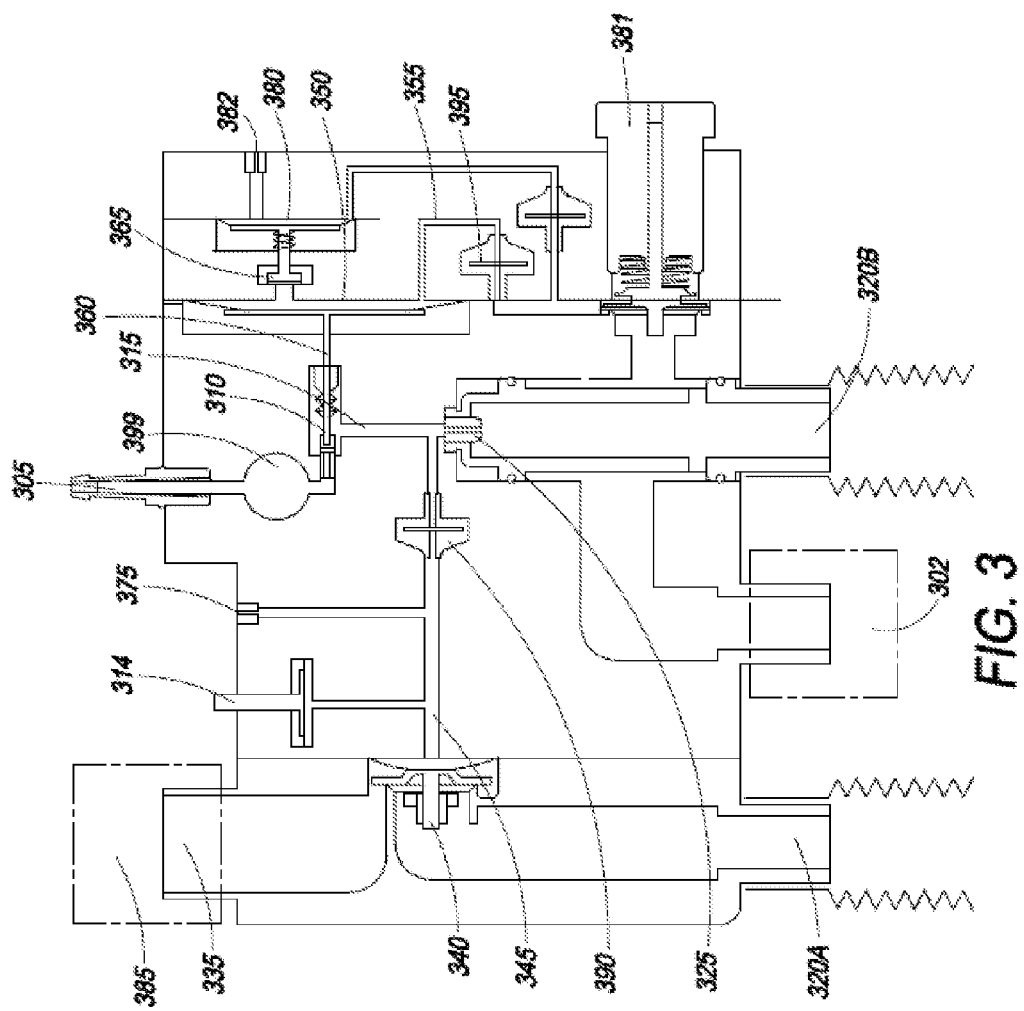
FIG. 3 is a schematic diagram of a first embodiment of the ventilator of the present invention.

The operational characteristics of the system components of FIG. 2 are described in detail with respect to FIG. 3. In addition, alarm circuit PCB 240, which in one embodiment is operably connected to the ventilator of the present invention via electronics actuator 214, is discussed in detail with respect to FIG. 4 below.

FIG. 3 is a schematic diagram of a first embodiment of the ventilator of the present invention. The operational characteristics of the first embodiment of the rapid response ventilator of the present invention will be described with respect to the schematic diagram of FIG. 3. It should be noted again that the operational descriptions below is exemplary and that language used in this specification should not be interpreted as a general disavowal of any one specific embodiment.

Referring now to FIG. 3, ventilator 300 comprises a compressed gas interface 305, which further comprises a compressed gas reservoir 399, which in use, is connected to a pressurized gas source (not shown). In one embodiment, the pressurized gas is oxygen. In another embodiment, the pressurized gas is medical compressed air. In one embodiment, compressed gas interface 305 is an inlet port.

Ventilator 300 further comprises gas control valve 310. Gas control valve 310 is connected to compressed gas reservoir 399 on one end. At the other end, gas control valve 310 is connected to inhalation conduit 315. Inhalation conduit 315 is operationally connected to patient interface 320 via flow control valve 325. In one embodiment, flow control valve 325 is a knob, capable of being manipulated to control breath rate. In another embodiment, flow control valve 325 is a fixed jet, delivering a breathing rate proportional to patient size.

In one embodiment, patient interface further comprises patient interface 320a for accepting air from the patient and patient interface 320b for delivering oxygen to the patient.

In one embodiment, patient interfaces 320a and 320b is connected to a breathing mask. In another embodiment, patient interfaces 320a and 320b are connected to an endotracheal tube. In yet another embodiment, patient interfaces 320a and 320b are connected to a laryngeal mask airway (LMA) device. Laryngeal mask airway devices are well-known to those of ordinary skill in the art and are used in anesthesia and emergency medicine for airway management. More specifically, it is a tube with an inflatable cuff that is inserted into the pharynx. It causes less pain and coughing than an endotracheal tube, and is easier to insert. It should be noted, however, that the laryngeal airway mask is not recommended for anyone at risk for lung aspiration.

Inhalation conduit 315, which is proximate to 320b, extends from patient interface 320b into an exhalation interface, which comprises exhaust port 335. Exhaust port 335 is controlled by expiratory valve 340, in communication with branch conduit 345 and connected to inhalation conduit 315, which is proximate to gas control valve 310. In one embodiment, a PEEP control mechanism is connected to expiratory valve 340. The PEEP control is then set, using external PEEP valve 385, as indicated by the patient's oxygenation indications.

In one embodiment, the ventilator of the present invention also comprises a pressure detector 314. In one embodiment, pressure detector 314 is employed as an interface to the alarm system described in FIG. 4. In one embodiment, pressure detector 314 is an electronic diaphragm actuator that translates activity within the ventilator into a signal that can be used to alarm the operator upon pre-determined events, as described in further detail below.

Diaphragm actuator 350 is connected to patient interface 320b via conduit 355 and non-return valve 395. Diaphragm actuator 350 is sealed to gas control valve 310, with push rod 360. Diaphragm actuator 350 can be sealed to gas control valve by any sealing means known to those of ordinary skill in the art, including, but, not limited to lip-sealing. Push rod 360 actuates the gas control valve 310 in response to the movement of diaphragm actuator 350. Diaphragm actuator 350 is also equipped with a servo valve 365, which is described in greater detail below.

In operation, a compressed gas is supplied to ventilator 300 from a source, such as a tank, preferably at a pressure greater than 5 PSI. In one embodiment, the compressed gas is oxygen. A gas regulator (not shown) regulates the delivery of compressed gas at a suitable pressure for use within the ventilator unit 300. In one embodiment, a suitable pressure for the compressed gas supply is in the range of 5 PSI to 60 PSI. In one embodiment, a suitable pressure for the compressed gas supply is 50 PSI. In another embodiment, a suitable pressure for the compressed gas supply is 30 PSI.

Inhalation is enabled by delivering regulated oxygen through gas control valve 310 and through inhalation conduit 315 and to flow control valve 325, thus increasing the pressure in inhalation conduit 315. The resultant back pressure in inhalation conduit 315, caused by flow control valve 325, is passed, via non return valve 390 to branch conduit 345, which subsequently actuates the expiratory valve 340. Once actuated, expiratory valve 340 seals exhaust port 335, enabling oxygen delivery to the patient and resulting in a pressure increase.

Diaphragm actuator 350 senses the resultant increase in pressure via non-return valve 395 and conduit 355 and causes push rod 360 to move up until gas control valve 310 is actuated, and thus closed, and gas flow is subsequently halted.

The pressure within diaphragm actuator 350 is retained by a servo valve 365. Servo valve 365 is controlled via servo diaphragm actuator 380. In particular, leak jet 382 reduces the pressure within servo diaphragm actuator 380 until the gas control valve 310 opens. When gas control valve 310 opens, servo valve 365 opens and subsequently discharges the gas pressure holding diaphragm actuator 350 in position, thus halting gas flow via flow control valve 325. When servo valve 365 is closed, oxygen flow resumes to the patient, thus repeating the cycle.

The initial back pressure responsible for closing expiratory valve 340 equalizes across flow control valve 325. The back pressure decays via leak jet 375, which controls the inspiration time, thus allowing expiratory valve 340 to open to the atmosphere. Exhalation is spontaneous when the over-pressure stored in the lungs during inhalation is released. The over-pressure in the lungs of the patient discharges through exhaust port 335, in the form of gas flow. In addition, leak jet 382 sets the expiratory time. Thus, the action of leak jets 375 and 382 set the breathing rate and therefore, the inhalation to exhalation ratio.

Referring back to FIG. 3, in one embodiment of the ventilator of the present invention, the expiratory time is preset to at least 1.5 seconds via adjusting the size of leak jet 382 and by adjusting the internal volume of servo diaphragm 380. In one embodiment, the expiratory time is preset to 2 seconds. In one embodiment of the ventilator of the present invention, the breathing rate is set in a range of between 10 and 45 Breaths per Minute (BPM).

In one embodiment of the present invention, the flow control valve or breathing rate control knob 325 is the only control that is required to be adjusted by the operator. The breathing rate control knob 325 can be adjusted to allow for various modes of operation, including but not limited to adult mode, pediatric mode, and infant mode.

In one embodiment, the ventilator of the present invention operates in Pressure Control Mode. In one embodiment of the present invention, airway pressure control 381, located proximate to patient interface 320b, is employed to set the target patient pressure in the control system. In one embodiment, the ventilation pressure is fixed and set by dimensions of diaphragm actuator 350 and the available settings of the regulator. In one embodiment, the pressure is suitable for most patients without causing any patient injury. In one embodiment, the ventilation pressure is variable and set by the operator. In one embodiment, the ventilator 300 operates in a range of 10 cm $H_2O$ to 70 cm $H_2O$. In another embodiment, ventilator 300 operates in a range of 20 cm $H_2O$ to 35 cm $H_2O$. In one embodiment, the ventilator 300 operates at a maximum of 20 cm $H_2O$. In another embodiment, the ventilator 300 can provide pressure-controlled ventilation at a pre-set pressure of 25 cm $H_2O$. Pressure relief valve 302 is located in the circuit to the patient that is set to ensure that over-pressure is not delivered to the patient.

In one embodiment, the ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel.

In one embodiment, the ventilator of the present invention is manufactured using tooling fabricated from a material of lower durability than steel at the onset of an epidemic. In one embodiment, the material of lower durability is aluminium. Preferably, the materials are readily accessible to produce a more limited number of units for more localized outbreaks of disease. The tooling can be manufactured fairly rapidly.

In one embodiment, the ventilator of the present invention is manufactured using parts that are fabricated in an automated system directly from design documentation. Thus, in this embodiment, no tooling is actually created. This embodiment is particularly useful for supporting remote areas where the ultimate goal is to transport patients to larger centres but temporary respiratory support is nevertheless required. Advantageously, the manufacturing method of the present invention allows for the ventilators to be produced on demand without the time it takes to manufacture the tooling.

In each of the manufacturing embodiments described above, assembly is simple and does not require highly specialized skills or training.

The ventilator can be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded.

In one embodiment of the rapid response ventilator of the present invention, the ventilator is capable of operating independent of electrical supplies.

In another embodiment, the rapid response ventilator is powered by oxygen at a regulated pressure.

In another embodiment the rapid response ventilator of the present invention is battery-operated.

In one embodiment, the rapid response ventilator of the present invention further comprises an alarm system.

In one embodiment, the rapid response ventilator of the present invention has an audio and/or visual alarm that alerts upon battery failure, or when the battery voltage falls below an acceptable pre-determined level. Thus, in one embodiment, the electronics of the alarm system are powered by a battery, such as a manganese-alkaline battery, a mercury type battery or any other suitable battery known to persons of ordinary skill in the art. When the battery voltage reaches a pre-determined, factory set voltage level a visual alarm is activated, such as the L.E.D. will start flashing in RED. Optionally, the alarm will also emit an audible alarm, such as a clicking sound. This is indicative that the battery needs to be changed. In one embodiment, the low battery voltage condition is set to sense when the battery voltage is less then 2.5 volts.

The alarm system is also capable of sensing the internal activity of the ventilator and upon sensing an alarm condition will provide a visual and/or audible output. In one embodiment, an alarm condition is low supply gas pressure. In another embodiment, an alarm condition is disconnection from the patient. In yet another embodiment, an alarm condition is failure to ventilate.

Thus, the alarm system is used to provide an audible and/or visual apnea alarm. In one embodiment, the alarm system causes an L.E.D. to emit a short flash, preferably green, with each breath to confirm that the ventilator system of the present invention is fitted and working properly. If no breaths are detected within a pre-determined time period, an audible and pulsating beep is emitted in conjunction with a flashing L.E.D., preferably RED, to identify that the alarm system of the ventilator of the present invention is in an alarm state. In one embodiment, the pre-determined time period between breath detection is factory pre-set and in the range of 15 to 20 seconds.

Figure 4:
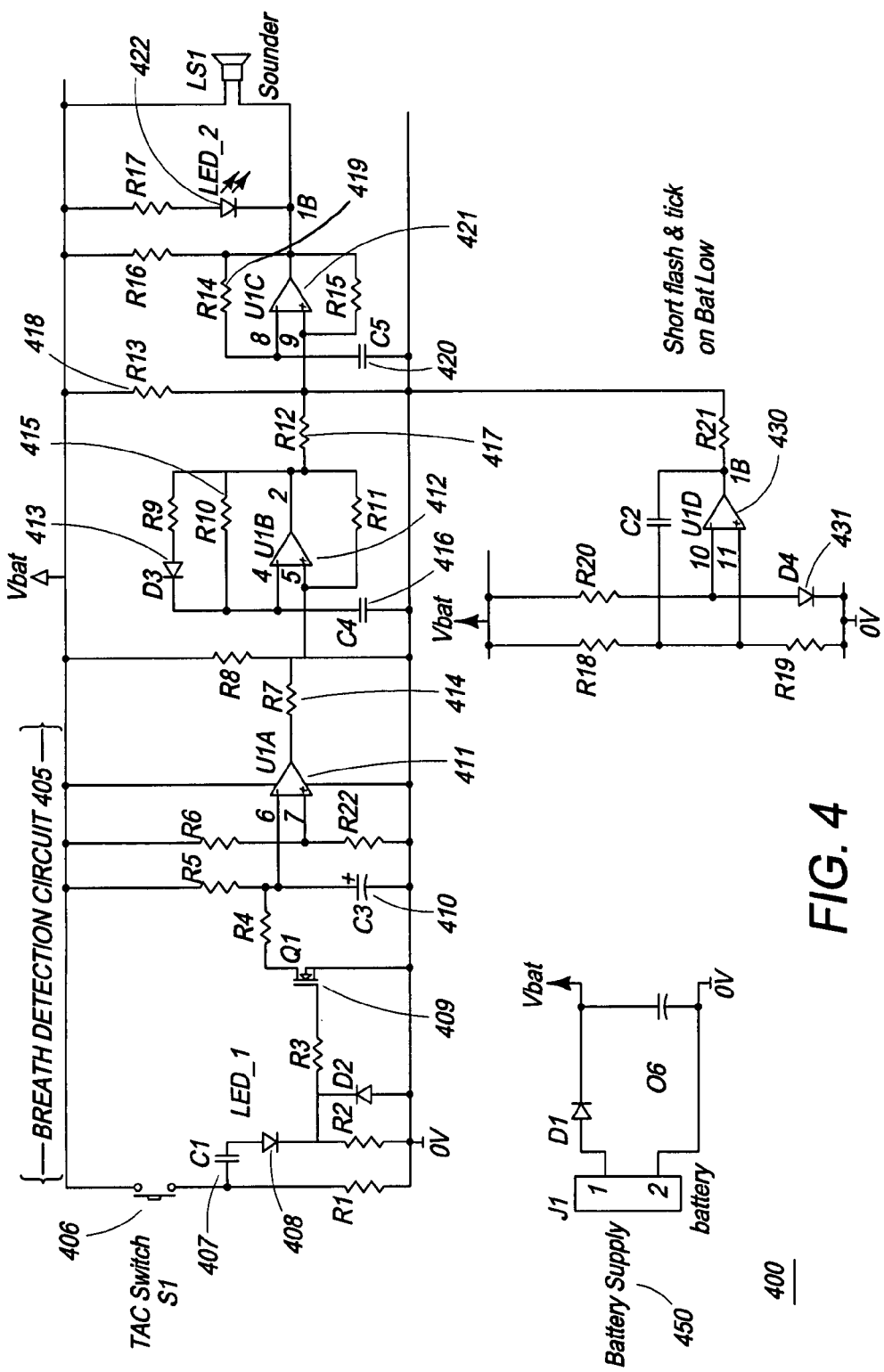
FIG. 4 is a schematic circuit diagram of one embodiment of an alarm circuit that is used in the ventilator of the present invention.

In one embodiment, as described above with respect to FIG. 3 and referring back to FIG. 3, the alarm system is operably connected to the ventilator of the present invention via an electronic diaphragm actuator 314. Specifically, the diaphragm actuator 314 is operably connected to a PCB (not shown), via a plunger on the electronics diaphragm actuator, which moves once per breath under the pneumatic action of the ventilator, and thus initiates sensing activity of the alarm system. The PCB also provides support for the power/battery components via connection to the battery terminals, as shown in FIG. 4. In addition, the audible alarm and LEDs are aligned with the ventilator system of the present invention to allow the sound and light to pass through such that they can operate as visible and audible alerts to the operator. In one embodiment, a change in pressure is detected by the diaphragm actuator which translates activity within the ventilator, into a signal that can be used by the PCB to alarm a pre-determined event, such as displacement of the diaphragm under pressure due to an increase in pressure.

In one embodiment, upon inhalation of the first breath by the patient, the battery supplies power to the alarm system so that it is deployed and thus, the alarm is ready to detect an alarm condition automatically on the occurrence of the first breath, minimizing the risk of an operator forgetting to deploy the alarm. Subsequent breaths alternate between inspiration during which air is supplied by the ventilator to the patient's lungs and expiration during which air passes out of the exhalation valve.

FIG. 4 is a schematic circuit diagram of one embodiment of the alarm circuit (PCB) as employed in the ventilator of the present invention. Referring back to FIG. 2, PCB 240 is employed to provide an alarm circuit to the ventilator system of the present invention. Referring now to FIG. 4, alarm circuit 400 is preferably formed on a printed circuit board that houses the electronic components. In one embodiment, alarm circuit 400 further comprises first stage breath detection circuit portion 405, which further comprises TAC Push Button Switch or membrane 406, which is actuated by the plunger of the electronics actuator (not shown), described with respect to FIG. 3. The plunger of the electronics actuator moves once per breath and thus, once per breath either "opens" or "closes" the TAC Switch 406, depending on orientation of the plunger.

In a first stage of the alarm circuit, when TAC Switch 406 closed and thus actuated, a pulse of current is passed through the circuit, via capacitor 407, and to LED 408 to generate the short confirming flash, described above. The flash decays as the capacitor 407 charges to minimize battery consumption. The peak current is set to provide a wetting effect for the contacts of switch 406. The transient current is detected by gate 409, which then switches on to discharge capacitor 410. If switch 406 does not close, or actuate, and thus remains open, then capacitor 410 will charge until the voltage on the negative input terminal of comparator 411 exceeds the voltage on the positive input terminal comparator 411. Subsequently, the open drain output pin 1 of comparator 411 switches to indicate and alarm condition. In one embodiment, comparator 411 is a dedicated voltage comparator chip.

The second stage of the alarm circuit 400 is an asymmetric oscillator. This oscillation signal provides the on-off modulation for the audible alarm, thus eliminating the need for the operator to distinguish the source of noise, especially in challenging and high background noise environments. When pin 1 of comparator 411 is low, the circuit thus oscillates to generate approximately pulses. The duty cycle and period is set by the values of resistors 414, 415 and capacitor 416. The duty cycle and period are factory set and may be adjusted if different periods and duty cycles are required. In one embodiment, the circuit oscillates to generate 100 msec pulses every 250 msec.

The third stage of alarm circuit 400 is an oscillator, which is, in one embodiment, fixed in the range of between 400 Hz and 1 kHz and provides the LED output upon alarm condition. When pin 2 of comparator 412 is low, the junction of resistors 417, 418 is brought to mid-rail and the oscillator is enabled. The nominal frequency is determined by the time constant of resistor 419 and capacitor 420. When the output of comparator 421 is low, the LED 422 flashes RED and the audible alarm is resonated at the nominal alarm frequency. The output from comparator 421 may, in one embodiment, be buffered if higher drive currents are needed by the particular audible alarm employed.

As mentioned above, alarm circuit 400 is also employed to monitor the battery voltage of battery 450. In one embodiment, comparator 430 is used to monitor the battery voltage against reference diode 431. If the divided voltage falls below the value of reference diode 431, then pin 12 of comparator 430 becomes low and enables the output oscillator described above. The output oscillator enables the short pulsing duration that causes the alarm to emit a periodic clicking noise to warn that the battery supply needs to be replaced.

The alarm system of the rapid response ventilator of the present invention is, in one embodiment, simple to manufacture and requires no calibration.

In one embodiment, the ventilator of the present invention can be operated for the expected duration of the peak of an epidemic.

In another embodiment, the ventilator of the present invention is single-patient use, preferably until the patient is weaned off the ventilator and is breathing independently.

In another embodiment, the ventilator is made of "green" materials and can be easily disposed of when it has been used on a single patient or when an epidemic has passed.

In a second embodiment, the present invention is a ventilator system that has control and range of operation so that it meets the needs of ARDS patients in various stages of a compromised state to recovery.

In addition, the present invention, in a second embodiment, is directed towards a ventilator that is capable of responding to varying patient needs quickly and effectively.

In addition, the present invention is directed towards a ventilator that is capable of meeting the needs of the ARDS patient ranging from a critical state until the patient can be safely weaned from the ventilator.

Most patients suffering from respiratory failure in a pandemic setting will meet the criteria for acute lung injury (ALI) or acute respiratory distress syndrome (ARDS). Current patient guidelines support the use of low tidal volumes (approximately 6 cc/kg ideal body weight) and the limitation of inspiratory plateau pressure (typically less than 30 cm $H_2O$) while maintaining adequate oxygenation, defined as arterial oxygen saturation of equal to or greater than 93%. Adequate oxygenation is provided by titration of supplemental inspired oxygen and PEEP.

In addition it is important to provide adequate minute ventilation by controlling arterial $PCO_2$, as assessed by an arterial pH of 7.3 to 7.4. Minute ventilation is the product of tidal volume and rate.

Figure 5:
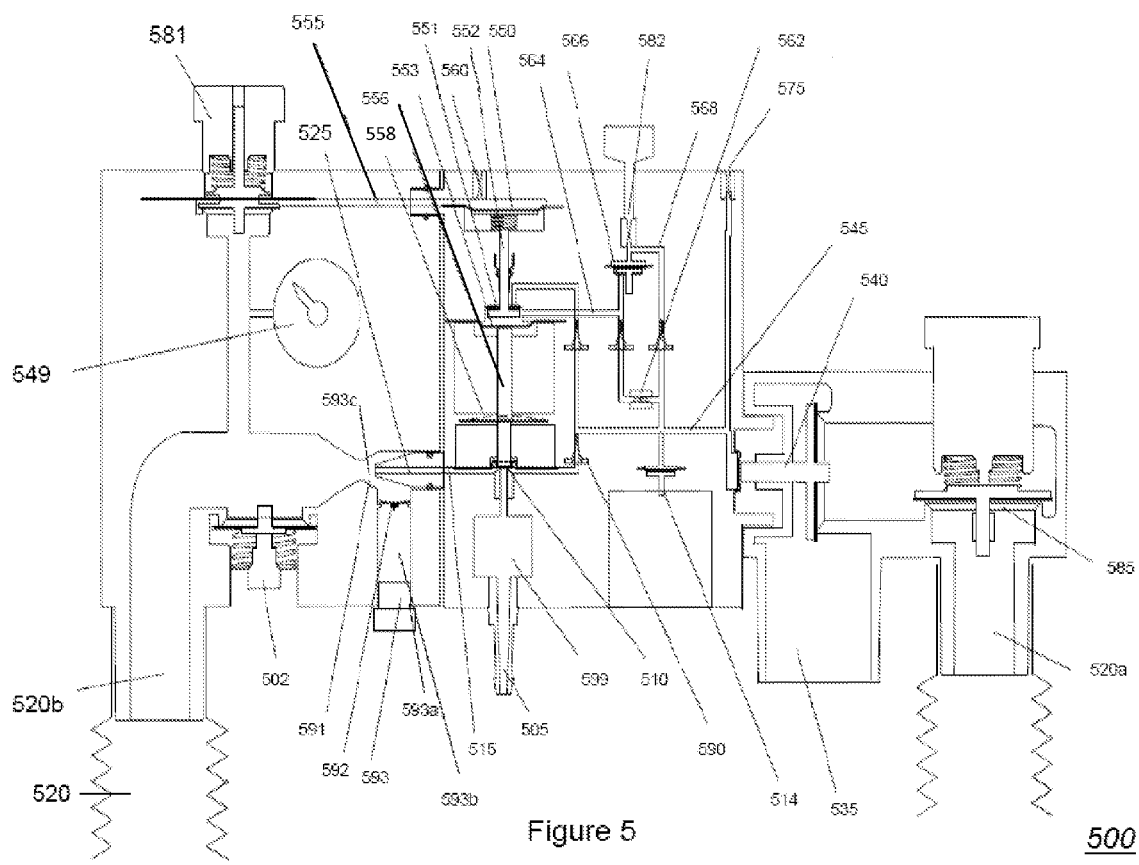
FIG. 5 is a schematic diagram of another embodiment of the ventilator of the present invention.

In an example of use of the second embodiment of the present invention, as shown in FIG. 5, a very ill patient may present with very severe hypoxemia, thus necessitating the use of high inspired oxygen levels. The high inspired oxygen level is denoted by $F_iO_2=1.0$, meaning that the percentage of oxygen in the inspired air is 100%. $F_iO_2$ represents the fraction of inspired oxygen, and ranges from 0 to 1.0.

To minimize the toxicity of oxygen, PEEP will be added at a rate of 5 cm $H_2O$, increasing in 5 cm increments up to a maximum of 15 cm $H_2O$. This results in the reduction of $F_iO_2$ while maintaining arterial oxygen saturation above 92%. As mentioned above, PEEP refers to the residual positive pressure that remains in the airway at the end of the expiratory cycle. It is employed to prevent the lung from fully collapsing after each breath, thus improving gas exchange in the lung.

Because the patient is very ill, he will likely have non-compliant (or stiff) lungs. Thus, the patient will initially require a high inspiratory pressure to achieve high tidal volumes, which in one embodiment, ranges from 30-35 cm $H_2O$. If the tidal volumes are small enough, the corresponding respiratory rate may be fairly high (25-30/min) to ensure adequate minute ventilation and carbon dioxide excretion. As the patient is improving, however, their lung compliance will increase, and the inspiratory pressure will need to be reduced (in the range of 10-15 cm $H_2O$, for example) to avoid over-distension of the lung. The target patient compliance range for the ventilator of the present invention is 20-50 cc/cm $H_2O$. In addition, as the patient improves, and gas exchange improves, less minute ventilation will be required to excrete carbon dioxide, so that the respiratory rate can also be reduced (in the range of 12-15 BPM, for example). Further, while the patient improves, the patient's oxygen requirements will also decrease, enabling a reduction in PEEP (to as low as 5 cm $H_2O$, for example), and a reduction in $F_iO_2$ (to 40% of its original level, for example). The ability to measure and titrate these variables improves the efficacy and safety of the mechanical rapid response ventilator of the present invention.

Thus, in a second embodiment of the ventilator of the present invention, the operator is able to manipulate the target airway pressure (PIP), PEEP, the level of oxygenation, and the respiration rate. The ventilator of the present invention can therefore more effectively be used in a broader cross-section of patients because it comprises additional controls.

Reference will now be made to a specific embodiment of the rapid response ventilator of the present invention having variable controls. It should be noted herein that while optimal ranges and values are provided, one of ordinary skill in the art should understand that each patient is different and that the mechanical ventilator of the present invention may be operated at levels suitable for a broad variety of patients.

FIG. 5 is a schematic diagram of a second embodiment of the ventilator of the present invention. Referring now to FIG. 5, ventilator 500 comprises a compressed gas interface 505, which further comprises a compressed gas reservoir 599, which in use, is connected to a pressurized gas source (not shown) via interface 505. In one embodiment, the pressurized gas is oxygen. In another embodiment, the pressurized gas is medical compressed air. In one embodiment, compressed gas interface 505 is an inlet port.

In operation, a compressed gas is supplied to ventilator 500 from a source, such as a tank, preferably at a pressure greater than 5 PSI. In one embodiment, the compressed gas is oxygen. A gas regulator (not shown) regulates the delivery of compressed gas at a suitable pressure for use within the ventilator unit 500. In one embodiment, a suitable pressure for the compressed gas supply is in the range of 5 PSI to 60 PSI. In one embodiment, a suitable pressure for the compressed gas supply is 50 PSI. In another embodiment, a suitable pressure for the compressed gas supply is 30 PSI.

Inhalation is enabled by delivering regulated oxygen through gas control valve 510 and through inhalation conduit 515 and to flow control valve 525, thus increasing the pressure in inhalation conduit 515. The resultant pressure in inhalation conduit 515, caused by flow control valve 525, is passed, via non return valve 590 to branch conduit 545, which subsequently actuates the expiratory valve 540. Once actuated, expiratory valve 540 seals exhaust port 535, enabling oxygen delivery to the patient and resulting in a pressure increase.

In one embodiment, the oxygenation level can be varied to provide a mixture of oxygen and air. In one embodiment, the control is variable, with three $O_2$/air ratio settings: 100%, 75%, and 50%. In another embodiment, the control is variable to provide two $O_2$/air ratio settings: 100% and 60%. This is achieved by an outside or atmospheric air entrainment area 591, which uses a venturi effect to deliver 60% oxygen, by physically receiving air through a conduit 593c. Conduit 593c has one end connected to input conduit 593b and a diameter equal to the input conduit 593c. As it reaches the air entrainment area 591, the diameter of conduit 593c narrows relative to the input conduit 593b. Atmospheric air enters the mechanism via a port 593a and a valve 592 that regulates air coming through the port 593a and travels to the air entrainment area 591 through a conduit 593b. The valve 592, which can be a non-return valve or a valve capable of being modulated, can be closed via cover 593, allowing 100% delivery of oxygen.

Ventilator 500 further comprises gas control valve 510. Gas control valve 510 is connected to compressed gas reservoir 599 on one end. At the other end, gas control valve 510 is connected to inhalation conduit 515. Inhalation conduit 515 is operationally connected to patient interface 520 via flow control valve 525.

In one embodiment, flow control valve 525 is actuated by a knob, capable of being manipulated to control breath rate. In another embodiment, flow control valve 525 is a fixed jet, delivering a breathing rate proportional to patient size.

In one embodiment, an optimal respiration rate is in the range of 15-35 BPM. In order to achieve a variable respiration rate, it should be noted that in one embodiment, the inspiratory time is fixed while the expiratory time is variable. For example, to achieve 20-35 BPM, the inspiratory time is fixed at 1 second while the expiratory time ranges from 0.8 to 2 seconds. In another example, to achieve 15-35 BPM, the inspiratory time is set to 1 second with a variable expiratory time range of 0.8 to 3 seconds ±0.1 second.

In one embodiment, the respiration rate control is an un-calibrated variable control. In another embodiment, the respiration rate control is an un-calibrated, detented control. In one embodiment, the control is labeled at its settable limits, such as low and high or such as low, medium, and high.

In one embodiment, patient interface 520 further comprises a patient interface 520a for accepting air from the patient and patient interface 520b for delivering oxygen to the patient.

In one embodiment, patient interfaces 520a and 520b are connected to a breathing mask. In another embodiment, patient interfaces 520a and 520b are connected to an endotracheal tube. In yet another embodiment, patient interfaces 520a and 520b are connected to a laryngeal mask airway (LMA) device. Laryngeal mask airway devices are well-known to those of ordinary skill in the art and are used in anesthesia and emergency medicine for airway management. More specifically, it is a tube with an inflatable cuff that is inserted into the pharynx. It causes less pain and coughing than an endotracheal tube, and is easier to insert. It should be noted, however, that the laryngeal airway mask is not recommended for anyone at risk for lung aspiration.

Inhalation conduit 515, which is proximate to interface 520b, extends from patient interface 520b into an exhalation interface, which comprises exhaust port 535. Exhaust port 535 is controlled by expiratory valve 540, in communication with branch conduit 545 and connected to inhalation conduit 515, which is proximate to gas control valve 5 10.

In one embodiment, a PEEP control mechanism is connected to expiratory valve 540. The PEEP control is then set, using PEEP valve 585, as indicated by the patient's oxygenation indications.

In one embodiment, PEEP is a variable control. In one embodiment, PEEP is variable from 5 cm $H_2O$ to 20 cm $H_2O$. In another embodiment, PEEP is variable from 10 cm $H_2O$ to 20 cm $H_2O$. In one embodiment, PEEP is a continuously variable control. In another embodiment, PEEP is controlled in increments of 5 cm $H_2O$. In one embodiment, at extubation, PEEP should be less than 10 cm $H_2O$ and more specifically, from 5-8 cm $H_2O$.

In one embodiment, the ventilator of the present invention also comprises a pressure detector 514. Pressure detector 514 is employed as an interface to the alarm system described in FIG. 4. Pressure detector 514 is an electronic diaphragm actuator that translates activity within the ventilator into a signal that can be used to alarm the operator upon pre-determined events, as described in further detail below.

Referring back to FIG. 5, in one embodiment, the ventilator of the present invention operates in Pressure Control Mode, thus the inspiratory time is controlled by pressure. In this embodiment, airway pressure control 581 is employed to set the target patient pressure in the control system. An integrated, pneumatic, inspiratory airway pressure gauge or monitor 549 is provided in the ventilator 500 of the present invention. The gauge is employed to display the instantaneous airway pressure value ranging from 0 to 50 cm $H_2O$.

Gas flows along conduit 555 and inflates diaphragm actuator 550. When actuator 550 is inflated, valve 551 is opened via push rod 552. This allows gas from conduit 545 to inflate diaphragm 553, which results in action by pushrod 556 and snap action dome spring 558, which results in the actuation of gas control valve 510, in response to the movement of diaphragm 550. Gas control valve 510 is closed to shut off gas supply. Leak jet 560 serves to allow diaphragm 550 to reset after actuation.

In some cases, as described above, a patient may exhibit a greater compliance (meaning that the patient is improving), and thus, the current setting of the pressure control of the inspiratory time could lead to over-inflation of the lungs. Therefore, the ventilator system of the present invention further comprises a timeout mechanism that limits the inspiratory flow. In one embodiment, the timeout mechanism limits inspiratory flow to approximately 0.9 seconds.

In one embodiment, the inspiratory flow can be set at a value in a range from a minimum value of 60 L/min to a maximum value of 100 L/min.

Referring back to FIG. 5, gas from conduit 545 flows through flow restrictor 562 and inflates diaphragm 553 via conduit 564, causing gas flow valve 510 to close, shutting off the gas flow.

After the gas flow has stopped via the closing of gas flow valve 510, leak jet 575 allows pressure in conduit 545 to dissipate, allowing expiratory valve 540 to open after a pre-set time interval. Conduit 564 is closed by valve 566, which is held closed by pressure in conduit 568.

Gas in conduit 568 is allowed to dissipate through valve 582. In addition, after the inspiratory flow is stopped, after a time interval that is set by pressure in valve 582, valve 566 is allowed to open, which vents conduit 564 and releases the pressure holding inspiratory valve 510 closed and the cycle restarts.

In one embodiment, the pressure is suitable for most patients without causing any patient injury. In one embodiment, the ventilation pressure is variable and set by the operator. In one embodiment, the ventilator 500 operates in a range of 10 cm $H_2O$ to 70 cm $H_2O$. In another embodiment, ventilator 500 operates in a range of 15 cm $H_2O$ to 40 cm $H_2O$. In one embodiment, the ventilator 500 operates at a maximum of 35 cm $H_2O$. In another embodiment, the ventilator 500 can provide pressure-controlled ventilation at a pre-set pressure of 25 cm $H_2O$. Pressure relief valve 502 is located in the circuit to the patient that is set to ensure that over-pressure is not delivered to the patient.

In one embodiment, the target airway pressure, or PIP, is a variable control and is labeled at its settable limits ranging from a minimum of 15 cm $H_2O$ and a maximum of 40 cm $H_2O$. In one embodiment, the PIP control further comprises a safety interlock, which is activated or interlocked at pressures above 35 cm $H_2O$.

The ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel.

The ventilator of the present invention can be manufactured using tooling fabricated from a material of lower durability than steel at the onset of an epidemic. In one embodiment, the material of lower durability is aluminum. Preferably, the materials are readily accessible to produce a more limited number of units for more localized outbreaks of disease. The tooling can be manufactured fairly rapidly.

In one embodiment, the ventilator of the present invention is manufactured using parts that are fabricated in an automated system directly from design documentation. Thus, in this embodiment, no tooling is actually created. This embodiment is particularly useful for supporting remote areas where the ultimate goal is to transport patients to larger centers but temporary respiratory support is nevertheless required. Advantageously, the manufacturing method of the present invention allows for the ventilators to be produced on demand without the time it takes to manufacture the tooling.

In each of the manufacturing embodiments described above, assembly is simple and does not require highly specialized skills or training.

The ventilator can be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded.

In one embodiment of the rapid response ventilator of the present invention, the ventilator is capable of operating independent of electrical supplies.

In another embodiment, the rapid response ventilator is powered by oxygen at a regulated pressure.

In another embodiment the rapid response ventilator of the present invention is battery-operated.

In one embodiment, the rapid response ventilator of the present invention further comprises an alarm system.

The rapid response ventilator of the present invention can also have an audio and/or visual alarm that alerts upon battery failure, or when the battery voltage falls below an acceptable pre-determined level. Thus, in one embodiment, the electronics of the alarm system are powered by a battery, such as a manganese-alkaline battery, a mercury type battery or any other suitable battery known to persons of ordinary skill in the art. When the battery voltage reaches a pre-determined, factory set voltage level a visual alarm is activated, such as the L.E.D. will start flashing in RED. Optionally, the alarm will also emit an audible alarm, such as a clicking sound. This is indicative that the battery needs to be changed. In one embodiment, the low battery voltage condition is set to sense when the battery voltage is less then 2.5 volts.

The alarm system is also capable of sensing the internal activity of the ventilator and upon sensing an alarm condition will provide a visual and/or audible output. In one embodiment, an alarm condition is low supply gas pressure. In another embodiment, an alarm condition is disconnection from the patient. In yet another embodiment, an alarm condition is failure to ventilate.

Thus, the alarm system is used to provide an audible and/or visual apnea alarm. In one embodiment, the alarm system causes an L.E.D. to emit a short flash, preferably green, with each breath to confirm that the ventilator system of the present invention is fitted and working properly. If no breaths are detected within a pre-determined time period, an audible and pulsating beep is emitted in conjunction with a flashing L.E.D., preferably RED, to identify that the alarm system of the ventilator of the present invention is in an alarm state. In one embodiment, the pre-determined time period between breath detection is factory pre-set and in the range of 15 to 20 seconds.

In one embodiment, as described above with respect to FIG. 5 and referring back to FIG. 5, the alarm system is operably connected to the ventilator of the present invention via an electronic diaphragm actuator 514. Specifically, the diaphragm actuator 514 is operably connected to a PCB (not shown), via a plunger on the electronics diaphragm actuator, which moves once per breath under the pneumatic action of the ventilator, and thus initiates sensing activity of the alarm system. The PCB also provides support for the power/battery components via connection to the battery terminals, as shown in FIG. 4. In addition, the audible alarm and LEDs are aligned with the ventilator system of the present invention to allow the sound and light to pass through such that they can operate as visible and audible alerts to the operator. In one embodiment, a change in pressure is detected by the diaphragm actuator which translates activity within the ventilator, into a signal that can be used by the PCB to alarm a pre-determined event, such as displacement of the diaphragm under pressure due to an increase in pressure.

In one embodiment, upon inhalation of the first breath by the patient, the battery supplies power to the alarm system so that it is deployed and thus, the alarm is ready to detect an alarm condition automatically on the occurrence of the first breath, minimizing the risk of an operator forgetting to deploy the alarm. Subsequent breaths alternate between inspiration during which air is supplied by the ventilator to the patient's lungs and expiration during which air passes out of the exhalation valve.

In another embodiment, the ventilator of the present invention is capable of responding to patient need. More specifically, in one embodiment, if a patient begins to resume breathing spontaneously, the ventilator of the present invention is capable of entering a passive mode. In another embodiment, if a patient fails to maintain spontaneous unassisted breath, the ventilator begins to operate and assist with oxygen delivery to the patient.

In one embodiment, the ventilator of the present invention is robust and can be operated even in situations where a patient is attempting to breathe. Thus, in one embodiment, the ventilator continues to operate normally and reliably in its controlled ventilation mode. The ability to adjust the respiration rate control to match the patient's respiration rate facilitates the robust use of the ventilator.

The above discussion is aimed towards providing several exemplary embodiments incorporating the novel aspects of the present invention and it should be understood that the foregoing illustration is not the only application where the present invention can be reduced down to practice. The present invention can be suitably modified to incorporate other possible embodiments as well. The scope of the invention is defined solely by the accompanying claims and within the scope of the claims; the present invention can be employed in various other situations.

The invention claimed is:

1. A controllable mechanical ventilator wherein said ventilator comprises:
   a gas input connected to a gas reservoir;
   an inhalation conduit connected to said gas reservoir for receiving gas and directing it to a patient interface;
   a flow control valve operable to control the flow of gas from the inhalation conduit to an air entrainment area, wherein said air entrainment area is connected, via a first conduit and a second conduit, to a port for receiving atmospheric air;
   the patient interface connected to said air entrainment area by a conduit; and
   a gas control valve, wherein said gas control valve is configured to close by a movement of a diaphragm actuator, a third valve and diaphragm, wherein said diaphragm actuator inflates in response to air flowing along a third conduit, wherein said third valve opens in response to the inflation of said diaphragm actuator, and wherein the opening of said valve causes air to flow in a fourth conduit which causes said at least one diaphragm to inflate which inflates in response to an increased pressure state and actuate said gas control valve.

2. The controllable mechanical ventilator of claim 1 wherein a valve is located in the first conduit to prevent air from passing out of the port and into the atmosphere.

3. The controllable mechanical ventilator of claim 1 wherein the second conduit has a first end connected to said first conduit and a second end connected to said air entrainment area and wherein the second conduit has a diameter that narrows from said first end to said second end, thereby having a diameter that is larger at said first end than at said second end.

4. The controllable mechanical ventilator of claim 1 wherein the amount of atmospheric air delivered through said patient interface can be modified by blocking said port.

5. A controllable mechanical ventilator wherein said ventilator comprises:
a gas input connected to a gas reservoir;
a patient flow control valve operably connected to control gas input from said gas reservoir via an inhalation conduit;
a patient interface separated from said inhalation conduit by said flow control valve;
a gas control valve, wherein said gas control valve is configured to close by a movement of a diaphragm actuator, a third valve and diaphragm, wherein said diaphragm actuator inflates in response to air flowing along a third conduit, wherein said valve opens in response to the inflation of said diaphragm actuator, and wherein the opening of said third valve causes air to flow in a fourth conduit which causes said diaphragm to inflate in response to a pressure state in and actuate said gas control valve;
wherein said ventilator is capable of responding to varying patient needs via at least one control.

6. A controllable mechanical ventilator wherein said ventilator comprises:
a gas input connected to a gas reservoir;
a patient flow control valve operably connected to control gas input from said gas reservoir via an inhalation conduit;
a patient interface, separated from said inhalation conduit by said flow control valve; and
a gas control valve, wherein said gas control valve is configured to close by a movement of a diaphragm actuator, a third valve and diaphragm, wherein said diaphragm actuator inflates in response to air flowing along a third conduit, wherein said valve opens in response to the inflation of said diaphragm actuator, and wherein the opening of said third valve causes air to flow in a fourth conduit which causes said diaphragm to inflate in response to a pressure state and actuate said gas control valve;
wherein said ventilator further comprises means for controlling at least one of: target airway pressure (PIP), positive end-expiratory pressure (PEEP), the level of oxygenation and respiration rate.

7. The ventilator of claim 6, wherein said ventilator further comprises a humidifying filter for trapping moisture and heat.

8. The ventilator of claim 6, wherein said ventilator comprises sterilizable material.

9. The ventilator of claim 6, wherein said patient flow control valve is adjustable to provide for a specific gas flow rate.

10. The ventilator of claim 9, wherein the gas flow rate can be set to at least one of adult, pediatric, and infant modes.

11. The ventilator of claim 6, wherein PIP is in the range of 20 cm $H_2O$ to 35 cm $H_2O$.

12. The ventilator of claim 6, wherein the gas input further comprises a gas interface for connection to a pressurized gas source.

13. The ventilator of claim 6, wherein the patient interface further comprises an interface for accepting exhaled gas from a patient and for delivering gas to the patient.

14. The ventilator of claim 6, wherein the patient interface is a breathing mask assembly.

15. The ventilator of claim 6, wherein the patient interface is an endotracheal tube.

16. The ventilator of claim 6, wherein the patient interface is a laryngeal mask airway device.

17. The ventilator of claim 6, wherein the flow control valve is in structural communication with a knob, capable of being physically manipulated to control breath rate.

18. The ventilator of claim 6, further comprising an expiratory conduit and expiratory valve operably connected to the patient interface.

19. The ventilator of claim 6, further comprising a pressure detector and an alarm circuit operably connected to the pressure detector, wherein said alarm circuit generates an alarm signal based upon a change in pressure detected by said pressure detector.

20. The ventilator of claim 6 wherein said patient flow control valve is operable to control the flow of gas from the inhalation conduit to an air entrainment area, wherein said air entrainment area is connected, via a first conduit and a second conduit, to a port for receiving atmospheric air.

21. The ventilator of claim 20 further comprising a fourth valve located in the first conduit to prevent air from passing out of the port and into the atmosphere wherein an oxygenation level can be varied by modulating said fourth valve to provide a mixture of oxygen and air.

22. The ventilator of claim 6 wherein the respiration rate is varied by keeping the inspiratory time fixed and varying the expiratory time.

23. The ventilator of claim 6 wherein PEEP is a variable control ranging from 5 cm $H_2O$ to 20 cm $H_2O$.

24. The ventilator of claim 6 wherein the ventilator further comprises an integrated pressure gauge, located proximate to the patient interface, for measuring and displaying the instantaneous airway pressure.

* * * * *